United States Patent [19]

Gillies

[11] Patent Number: 5,665,578
[45] Date of Patent: Sep. 9, 1997

[54] VECTOR AND METHOD FOR ACHIEVING HIGH LEVEL OF EXPRESSION IN EUKARYOTIC CELLS

[76] Inventor: Stephen D. Gillies, 145 Gilson Rd., Scituate, Mass. 02066

[21] Appl. No.: 223,381

[22] Filed: Apr. 5, 1994

Related U.S. Application Data

[63] Continuation of Ser. No. 879,700, May 5, 1992, abandoned, which is a continuation of Ser. No. 635,799, Jan. 2, 1991, abandoned, which is a continuation of Ser. No. 837,595, Mar. 7, 1986, abandoned.

[51] Int. Cl.$^6$ .............. C12N 5/10; C12N 15/63; C12N 15/64
[52] U.S. Cl. .............. 435/172.3; 435/320.1; 435/325; 435/354; 435/355
[58] Field of Search ............... 435/69.1, 70.1, 435/172.1, 172.3, 240.1, 240.2, 320.1; 536/24.1

[56] References Cited

U.S. PATENT DOCUMENTS

| | | | |
|---|---|---|---|
| 4,349,629 | 9/1982 | Carey et al. | 435/172.3 |
| 4,371,625 | 2/1983 | Tiollais | 435/320.1 |
| 4,374,927 | 2/1983 | Sninsky et al. | 435/69.1 |
| 4,399,216 | 8/1983 | Axel et al. | 435/6 |
| 4,405,712 | 9/1983 | Vande Woude et al. | 435/5 |
| 4,418,149 | 11/1983 | Ptashne et al. | 435/252.33 |
| 4,663,281 | 5/1987 | Gillies et al. | 435/69.1 |
| 4,740,461 | 4/1988 | Kaufman | 435/69.1 |
| 4,931,373 | 6/1990 | Kawasaki et al. | 435/69.2 |
| 5,001,230 | 3/1991 | Brown et al. | 536/23.5 |

FOREIGN PATENT DOCUMENTS

| | | |
|---|---|---|
| 0011562 | 5/1980 | European Pat. Off. |
| 0052002 | 11/1981 | European Pat. Off. |
| 0064681 | 4/1982 | European Pat. Off. |
| 0067540 | 6/1982 | European Pat. Off. |
| 0072925 | 7/1982 | European Pat. Off. |
| 0076037 | 8/1982 | European Pat. Off. |
| 0077689 | 10/1982 | European Pat. Off. |
| 2100738 | 6/1982 | United Kingdom . |
| 2105344 | 3/1983 | United Kingdom . |
| 8102425 | 2/1981 | WIPO . |
| 8200158 | 7/1981 | WIPO . |
| 8300702 | 8/1982 | WIPO . |

OTHER PUBLICATIONS de Villiers et al. 1982. Cold Spring Harbor Symp. Quant. Biol 47:911–919.
Browne et al. 1985. Gene 33:279–284.
Mulligan et al. 1981. PNAS 78:2072–2076.
"Expression of a Beta–Globin Gene is Enhanced by Remote SV40 DNA Sequences" Banerji et al. Cell. vol. 27, 299–308, Dec. 1981 (Part 1).
"A Lymphocyte–Specific Cellular Enhancer is Located Downstream of the Joining Region in Immunoglobin Heavy Chain Genes" Banerji et al. Cell. vol. 33, 729–740, Jul., 1983.
"Interaction Between Host and Viral Genomes in Mouse Mammary Tumors" Bentzelzen Ann. Rev. Genet. 1982 16:273–95.
"Enhancer Elements in Immunoglobulin Genes", Michael A. Boss Nature vol. 303 26 May 1983, pp. 281–282.
"Isolation and Characterization of Human DNA Fragments with Nucleotide Sequence Homologies with the Simian Virus 40 Regulatory Region" Conrad et al., Molecular and Cellular Biology, Aug. 1982, pp. 949–965, vol. 2 #8.
"A Small Segment of Polyoma Virus DNA Enhances the Expression of a Cloned Beta–Globin Gene Over a Distance of 1400 Base Pairs" deVillieres and Schaffner, Nucleic Acids Research vol. 9, No. 23, 1981, p. 6251.
"A Tissue–Specific Transcription Enhancer Element is Located in the Major Intron of a Rearranged Immunoglobulin Heavy Chain Gene" Gillies, et al., Cell. vol. 33, 717–728, Jul. 1983.
"Mud(Ap. lac)–Generated Fusions in Studies of Gene Expression", Krueger and Walker, Methods of Enzymology, vol. 100, p. 501.
"Host–Specific Activation of Transcription by Tandem Repeats from Simian Virus and Moloney Murine Sarcoma Virus" Laimins et al., Natl. Acad. Sci. USA, vol. 79, pp. 6453–6457, Nov. 1982.
"Immunoglobulin Genes Have Enhancers", Marx. Research News, Aug. 19, 1983, pp. 735–737.
"The SV40 72 Base Repair Repeat has a Striking Effect on Gene Expression Both in SV 40 and other Chimeric Recombinants" Moreau et al., Nucleic Acids Research, vol. 9 No. 22, 1981.
"Multiple Point Mutations Affecting the Simian Virus 40 Enhancer" Weiher et al., Science vol. 219, Feb. 11, 1983, pp. 626–631.

*Primary Examiner*—Mindy Fleisher
*Assistant Examiner*—Terry A. McKelvey
*Attorney, Agent, or Firm*—Testa, Hurwitz & Thibeault LLP

[57] ABSTRACT

Disclosed are vectors for achieving high level expression in eucaryotic cells. The vectors include an expressible gene encoding a protein product of interest, an expressible gene encoding a marker protein which permits selection of useful transformants, and an enhancer element, preferably a cellular enhancer element, which functions to increase the level of transcription of genes disposed on its 3' and 5' sides. A blocking element is interposed between the enhancer element and the marker gene which shields the promoter of the marker gene from the transcription-stimulating function of the enhancer, thereby limiting the effect of the enhancer to transcriptions of the DNA encoding the protein product of interest. Use of the vectors permits isolation of viable clones characterized by a very high level of expression of the protein of interest.

9 Claims, 9 Drawing Sheets

VECTOR AND METHOD FOR ACHIEVING HIGH LEVEL OF EXPRESSION IN EUKARYOTIC CELLS

This is a continuation of application Ser. No. 07/879,700 filed on May 5, 1992, abandoned, which is a continuation of Ser. No. 07/635,799 filed on Jan. 2, 1991, abandoned, which is a continuation of Ser. No. 07/837,595 filed Mar. 7, 1986, now abandoned.

BACKGROUND OF THE INVENTION

This invention relates to expression vectors for transfecting eucaryotic cells to produce transformants having a high level of expression of a protein of interest.

Gillies et al disclose in Cell, Vol. 33, pp. 717–728, Jul., 1983 and in more detail in copending U.S. application Ser. No. 592,231 filed Mar. 22, 1984 now U.S. Pat. No. 4,663,281, the disclosure of which is incorporated herein by reference, that specialized animal cells of the type which produce large quantities of a secreted protein such as globulins, fibrinogen, albumin, etc. exploit a tissue specific enhancer element present in their genome near the promoter and the gene encoding the protein. These cellular enhancer elements significantly enhance expression of a gene when located on either the 5' or 3' side of the gene. The functioning of this type of cellular enhancer is independent of the enhancer's orientation, and its ability to promote transcription from either homologous animal gene promoters or heterologous viral promoters is observed even when the enhancer element is disposed 10 kilobases (kb) or further away from the promoter.

The above-referenced Gillies et al application discloses methods of isolating such cellular enhancer elements from the genomes of animal cells and methods of exploiting their function in the construction of vectors designed to achieve expression of specific genes. The vectors may be used to transfect cells derived from the same tissue type in which the enhancer's activity is displayed naturally to produce valuable proteins. Transformants containing recombinant DNA including a cellular enhancer element and recombinant transcription unit such as a promoter ligated to a cDNA are characterized by high levels of transcription and translation of the cDNA and therefore significant improvements in expression.

The construction of chimeric viral and/or plasmid vectors containing such cellular enhancer elements has confirmed that these elements stimulate transcription of genes and promoters 10,000 base pairs or more from either the 5' or 3' end of the enhancer segments. Since stable, replicatable vectors typically comprise no more than about 20,000 base pairs, after transfection the enhancer stimulates transcription not only of the gene encoding the protein of interest, but also the gene encoding the marker protein which is used in the isolation of cells which have successfully incorporated the recombinant DNA.

It has been discovered that this link between expression of the marker protein and the protein of interest can limit the expression of the protein of interest. Transformants containing the recombinant plasmid typically are selected by culturing the cells in the presence of one or more toxic components. Only those cells which have been transformed by the recombinant vector and which express appropriate levels of the marker protein survive. Transfected cells expressing too low a level of the marker protein will not survive. Equally important, transfected cells expressing too high a level of the marker protein may also not survive. This is because too high a level of the marker protein may interfere with the cell's normal metabolism. Thus, transformed cells expressing very high levels of the protein of interest may be difficult to obtain because the concomitant high expression of the marker protein may be lethal.

An ideal expression system would uncouple the expression of the marker protein from the enhanced expression of the protein of interest. With such a system, transformed cells expressing levels of the marker protein appropriate for survival could express higher levels of the protein of interest than was previously possible.

SUMMARY OF THE INVENTION

The invention features expression vectors constructed such that the cellular enhancer element of the type described above is active to promote high levels of expression of a desired gene encoding a protein product, but does not significantly affect the level of expression of the marker protein. This enables production of transformants which produce high levels of a desired protein while producing the marker protein only at levels required for selection.

The approach of the invention is to interpose between the cellular enhancer and the transcription unit encoding the marker protein a DNA comprising nucleotides having the function of blocking the stimulating effect of the enhancer element on the marker gene. It has been observed that the activity of the enhancer element is dissipated by flanking promoter sequences. Accordingly, vectors of the invention employ a promoter sequence, or a DNA having substantial homology with a promoter sequence, interposed between the enhancer element and the promoter of the marker gene to block the enhancement effect on the marker gene's promoter. The term "blocking element", as used herein, refers collectively to intact DNAs having an observable transcription-promoting function, various restriction fragments of such promoter sequences, and other natural or synthetic polynucleotides which serve to dissipate the enhancer element's promoter-stimulating effect.

In one preferred embodiment, the blocking element is a promoter sequence oriented in the vector with its native 3' end disposed proximal to the enhancer element and its native 5' end disposed distal to the enhancer element. Such a reverse orientation of a promoter sequence disposed adjacent the enhancer element efficiently inactivates enhanced promotion of transcription of the marker gene. In this embodiment, and in each subsequent embodiment and description of the invention, the orientation of the 5' and 3' ends of the double stranded DNA molecule are stated with respect to a 5' to 3' direction of transcription. In another preferred embodiment, the interposed blocking element comprises a promoter sequence with its 5' end disposed proximal to the enhancer element and, at its 3' end, a gene encoding a desired protein. If desired, a second enhancer element may be interposed between the the promoter sequence and the first enhancer element. This type of construct results in a vector in which two proteins of interest may be expressed, or in which the same protein may be expressed from separate transcription units.

The isolation of clones of transformed cells expressing high levels of the protein of interest is a two-step process. The first step is a selection step in which only those cells transfected with the marker gene and expressing appropriate levels of the marker protein survive in medium containing a toxic component. The second step is a screening process in which the transformed cells are assayed for production of the protein of interest. The production of stably transformed cells is generally thought to require the integration of the recombinant plasmid into the genome of the cell by means of a double strand breakage of the vector DNA and religation at a double strand break in genomic DNA. If the vector DNA breaks within a gene during integration, the activity of that gene will be lost. Because selection requires the expression of the marker protein, none of the transformants will have integrated a vector severed within the marker gene. However, there is no selection against integration within, and therefore inactivation of, the gene coding for the protein of interest. Thus, transformed cells must be screened to identify those which express the protein of interest. Because the activity of the cellular enhancer element is exerted only on the gene(s) of interest in vectors constructed in accordance with the invention, transformants may be obtained which express the protein of interest at high levels.

More specifically, the expression vectors of the invention comprises 1) DNA defining an enhancer element of the type which is operative to enhance promotion of transcription of genes located in regions on both the 5' and 3' sides of the enhancer element; 2) DNA defining a transcriptionally competent marker region comprising a promoter and a gene encoding a selectable marker protein located in a region on one side of the enhancer element; 3) DNA defining a transcription unit, including a promoter and a gene encoding a protein product, located in a region on the other side of the enhancer element at a distance from the enhancer element sufficient to permit enhancement of expression of the transcription unit; and 4) DNA defining a blocking element interposed between the enhancer element and the marker region operable to block enhancement of transcription of the gene encoding the selectable marker. Alternatively, the vector may comprise a construct including DNA defining a restriction site, disposed adjacent the 3' end of a promoter, for ligating a gene encoding a desired protein product. Such constructs may be used to fabricate expression vectors for producing various proteins by ligating a selected gene encoding the protein within the restriction site.

In preferred embodiments, the blocking element is a substantially intact promoter sequence oriented in the vector with its native 3' end disposed proximal to the enhancer element and its native 5' end disposed distal to the enhancer element. Alternatively, the promoter sequence may be disposed adjacent a gene encoding the same or a different protein of interest. Preferably, vectors of the invention comprise plasmid or viral DNA.

BRIEF DESCRIPTION OF THE DRAWING

FIGS. 9A-9D disclose the complete nucleotide sequence of vector pEMpl-tpa; and

Like reference characters in the respective drawn figures indicate corresponding elements.

DESCRIPTION

Figure 1:
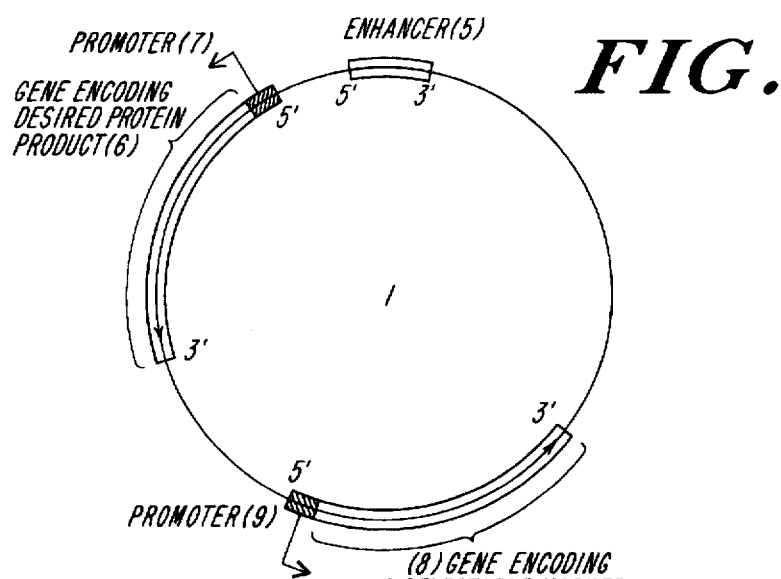
FIG. 1 depicts an expression vector useful in describing the differences between vectors of the invention and previously constructed vectors.

The invention provides vectors comprising components which make them suitable for transfection into selected, preferably continuous, animal cell lines to obtain continuously culturable transformants characterized by a high level of expression of a protein of interest. Methods of identifying and isolating genes encoding proteins of interest, or for constructing such genes, are now well understood and developed. The literature describes numerous methods useful in obtaining genes encoding various potentially or demonstrably useful proteins such as lymphokines, cytokines, immunoglobulins, hormones, enzymes, and vaccines. Vectors of this invention may be used to produce monoclonal cultures which produce urokinase, prourokinase, tissue plasminogen activator, various blood clotting factors, other useful enzymes, antibodies, hormones, and various other types of proteins for clinical, diagnostic, and other uses.

It should be noted at the outset that the vector construction principles disclosed herein can be exploited using now well known and well developed construction techniques involving the use of various restriction enzymes which make sequence-specific cuts in DNA to produce blunt ends or cohesive ends. DNA ligases, techniques enabling enzymatic addition of sticky ends to blunt-ended DNA molecules, cDNA synthesis techniques, synthetic probes for isolating genes having a particular function, conventional transfection techniques, and equally conventional techniques for cloning and subcloning DNA. Various types of vectors may be used such as plasmids and viruses including animal viruses and phages. Also, the vectors of the invention may exploit various marker genes which impart to a successfully transfected cell a detectable phenotypic property which can be used to identify which of a family of cells have successfully incorporated the recombinant DNA of the vector. The expression vectors of the invention are preferably used in animal cell lines. A preferred marker is a transcription unit which encodes an enzyme normally not expressed (or expressed only at low levels) by the cells which enables the cells to survive in a medium containing a toxic component. Examples of such enzymes include thymidine kinase (TK), adenosine phophoribosyltransferase (APRT), and hypoxanthine phosphoribosyl transferase (HPRT), which enable TK, APRT, or HPRT-deficient cells, respectively, to grow in hypoxanthine/aminopterin/thymidine medium; dihydrofolate reductase (DHFR), which enables DHFR-deficient cells to grow in the presence of methotrexate; the *E. coli* enzyme xanthine-guanosine phosphoribosyl transferase (XGPRT, the product of the gpt gene), which enables normal cells to grow in the presence of mycophenolic acid; and the procaryotic enzyme Tn5 phosphotransferase, which enables normal cells to grow in the presence of neomycin. Other suitable marker genes will be useful in the vectors of the invention.

All of the vectors of the invention include an enhancer element of the type which acts on promoters disposed on both the 5' and 3' end of the enhancer element, or spaced apart from either end, to enhance transcription of genes located on the 3' end of the promoters. The enhancer element may include DNA of vital origin such as those disclosed by Banerji et al. (Cell, V. 27, 299–308, 1981), deVilliers and Shaffner (Nucl. Acids Res., V. 9, 6251–6264, 1981), or Levinson et al. (Nature, V. 295, 568–572, 1982), but preferably is a cellular enhancer element of the type recently discovered by Gillies and Tonegawa and disclosed in Cell, (V. 33, 717–728 1983), and in more detail in U.S. Pat. No. 4,663,281. Investigation of a number of such cellular enhancers has shown that they have core sequences in common with viral enhancers. The most important characteristic of cellular enhancers is their cell-type or tissue-type specificity. Thus, the transcription-enhancing function of a cellular enhancer will be observed only if the enhancer is present in an animal cell from the particular tissue type wherein the enhancer is normally active.

Cellular enhancers active in particular types of eucaryotic cells are present in association with transcription units encoding some of the various proteins produced by the cells. However, since the entire genome of an individual is present in most of the cells of the individual, enhancers may be derived from almost any cell of the individual or from a genetic library. DNA fragments containing enhancer activity which are reduced in size with restriction enzymes lose their enhancer function progressively. Intact cellular enhancer element sequences are often a thousand or more base pairs in length, but residual enhancer activity can often be found in significantly shorter fragments.

A useful approach to identifying and isolating an enhancer useful in a selected cell type, e.g., a lymphoid cell, is to identify the gene for a protein produced in abundance by the lymphoid cell and to subclone restriction fragments of the gene and its flanking regions into a vector at a location reasonably close to some expressible DNA. The recombinant vectors are then transfected into cells of the selected cell type (here lymphoid cells), and the cells are assayed to determine which if any are producing the protein encoded by the expressable DNA at enhanced levels. Any such recombinant containing the enhancer element may be used as a source of enhancer element for constructing vectors useful in the practice of this invention. Thus, in the context of the instant invention, the term "enhancer element" as used herein refers to a trans-acting element encoded by a DNA sequence of cellular origin which acts on promoters disposed on both its 5' and 3' ends, or spaced apart from either end, to stimulate transcription of genes located on the 3' end of said promoters. While intact cellular enhancer element sequences may be in excess of a thousand base pairs in length, residual transcription stimulation activity is often found in significantly shorter fragments. The term "enhancer element" as used herein also contemplates such fragments which retain enhancer activity.

A preferred screening method involves construction of a "test vector". Such a vector imparts a phenotypic characteristic, e.g., resistance to a cell toxin, necessary for cell survival in a screening medium only if, before transfection, an enhancer active in the cell has been recombined into the vector. Such vectors can be constructed by deleting from a known vector the vital enhancer sequences normally associated with expression of the phenotype such that the deletion vector is no longer effective to impart the phenotype. Restriction fragments of the test gene and its flanking regions suspected to contain an enhancer are then inserted into the deletion vector, the recombinants are transfected into the cell line, and the cells are cultured in the presence of the toxin. In this circumstance, only clones containing recombinants which include an enhancer element operative in the cell line will survive. This results in a culture of cells which must have the phenotype and accordingly must have an enhancer effective in the cells.

The enhancer is then excised from these recombinant vectors and recombined with a transcription unit encoding a protein of interest in the same or a different vector. Vectors including an enhancer element may be constructed using conventional techniques. They may be constructed from phages, animal or other viruses, or plasmids using conventional restriction enzymes, ligases, and other methodology. Vectors and transfection procedures resulting in stably transformed cells are preferred. The vectors comprise a DNA segment containing the enhancer function ligated to a DNA segment including a transcription unit, i.e., one or more exons and a promoter.

The concept on which this invention is based is best understood by reference to the drawing. FIG. 1 depicts a generalized vector 1 which may comprise plasmid or viral DNA recombined with exogenous DNA by conventional construction techniques to produce a vector for expressing a gene encoding a desired protein product. The vector includes sequences derived from the native plasmid or virus necessary for its replication in procaryotic cells. In addition, it includes an enhancer element 5, a gene encoding a desired protein product 6 and its associated promoter 7, and a transcriptionally competent marker region comprising a gene encoding a selectable marker 8 and its associated promoter 9. The total number of base pairs (bp) in vector 1 normally will not exceed 20,000, and typically is on the order of 10,000 bp or less.

Since the enhancer 5 has the ability to stimulate transcription of transcription units disposed on both its 3' and 5' sides, the enhancer, after transfection, will be active to stimulate both promoter 7 to result in enhanced transcription of the gene encoding a protein product 6, and to stimulate promoter 9 to enhance transcription of the marker gene 8. While RNA polymerase initiates RNA synthesis at the 5' end of a promoter and proceeds toward the 3' end of the gene, the effect of the enhancer is observed irrespective of the orientation or position of either transcription unit in the vector. Thus, high levels of mRNA corresponding to the marker gene and the protein product are observed even if the orientation of the unit comprising the promoter 9 and marker gene 8 is reversed, the promoter 7 and protein product gene 6 is reversed, or the positions of the respective transcription units are reversed in sequence in the vector. Thus, the effect of the presence of the enhancer is transmitted (by mechanisms unknown) both clockwise and counterclockwise (see FIG. 1) to stimulate both promoter 7 and promoter 9.

While this vector can be successfully incorporated into a cell, as identified by display of the phenotypic characteristic imparted by selectable marker 8, in many cases that cell will exhibit an enhanced level of transcription of both marker gene 8 and the protein product gene 6. Such transformants will produce proteins encoded by both genes at high levels. Where the marker results in expression of an enzyme which makes the cell resistant to a toxin, the high level expression may place the monoclonal culture at a competitive disadvantage because, depending on the type of marker used, it may tend to interfere with the cell's normal metabolism. In any case, high level production of both proteins complicates purification of the desired protein product. Thus, while the enhancer increases expression of both the marker gene and the gene of interest, when the marker gene encodes an enzyme that enables cell survival in a toxic medium, the selection procedure may eliminate transformants expressing very high levels of the marker protein, thereby precluding the isolation of transformants expressing very high levels of the protein of interest.

The way to overcome the foregoing problem is based on the discovery that the stimulating effect of the enhancer element is dissipated on a promoter, irrespective of its orientation, and whether or not the promoter is present together with a gene. The vectors of the invention accordingly include a blocking element interposed between the enhancer and the transcription unit comprising the marker region such that transcription of the marker region gene is not enhanced.

Use of such vectors inherently enables the isolation of transformants which produce the marker protein at relatively low but detectable levels, levels sufficient to confer viability, yet display enhanced, high level transcription of the gene encoding a protein product. Thus, the level of expression of the protein of interest relative to that of the marker protein will increase when enhancement of the marker protein is blocked.

Accordingly, the term "enhanced level of expression" as used herein refers to production of a desired heterologous protein by the instant invention's transfected cell line at a concentration which is elevated relative to the concentration of the selectable marker protein.

Figure 2:
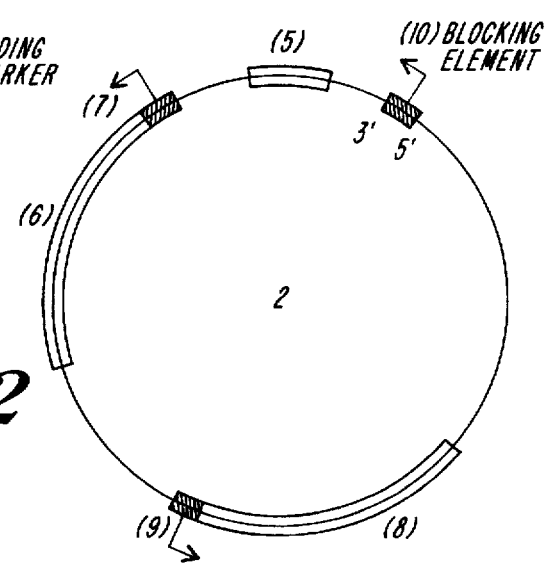
FIGS. 2 through 6 are diagrams illustrating vectors comprising embodiments of the invention.

FIGS. 2–6 illustrate various vectors embodying the invention. The vector of FIG. 2 is similar to vector 1 except that a blocking element 10 is interposed between the DNA comprising the marker region and its promoter and the DNA comprising enhancer 5. Blocking element 10 may consist of DNA comprising a promoter sequence or a promoter restriction fragment. Any promoter may be used as a blocking agent. In the embodiment of FIG. 2, the promoter or promoter-like sequences constituting blocking element 10 are disposed adjacent enhancer 5 and oriented with its 3' end proximal and its 5' end distal to enhancer 5. Since there is no expressable DNA interposed between blocking element 10 and enhancer 5, even if the element 10 comprises an intact promoter, it cannot serve to initiate transcription of mRNA. However, it has been discovered that it does serve to dissipate the promoter-stimulating action of enhancer 5 such that the enhancer has negligible or no effect on the promoter 9 for the marker gene 8.

The effect of the enhancer 5 in the opposite direction is to stimulate the promoter 7 to produce enhanced quantities of mRNA transcribed from the gene encoding a desired protein product 6. Again, the stimulating effect of the enhancer 5 is dissipated on promoter 7 such that the promoter 9 of marker gene 8 remains unaffected.

Figure 3:
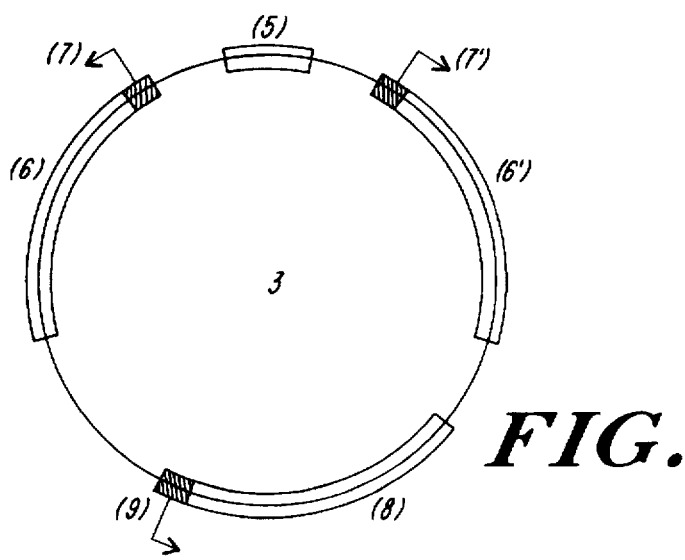

FIG. 3 illustrates another embodiment of the invention wherein an enhancer 5 is flanked by a pair of transcription units comprising promoters 7 and 7' and associated genes encoding a desired protein product 6 and 6'. The promoters 7 and 7' need not necessarily be the same promoter. Similarly, the expressible DNAs 6 and 6' may encode the same or different protein products. The presence of these flanking transcription units effectively shields promoter 9 and its gene 8 from the enhancing activity of enhancer 5.

Figure 4:
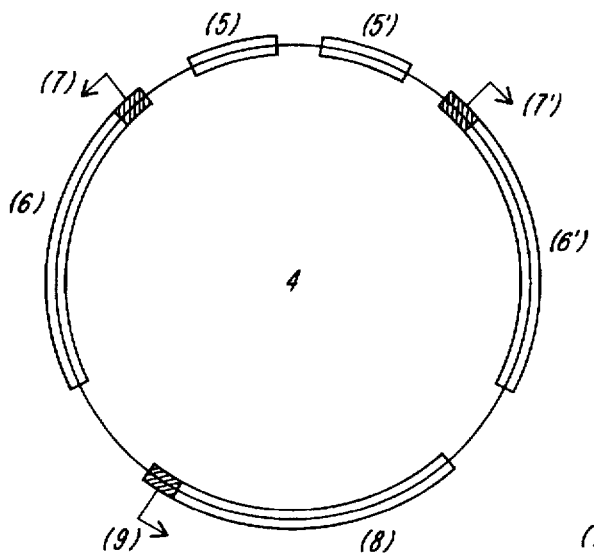

FIG. 4 illustrates still another vector embodying the invention. It comprises a pair of enhancer elements 5, 5' disposed between a pair of transcription units. Transformants successfully incorporating DNA from this vector produce large quantities of mRNA transcribed from genes 6 and 6' because of the combined effect of the dual promoter sequences, but much smaller amounts of the protein encoded by marker gene 8.

Figure 5:
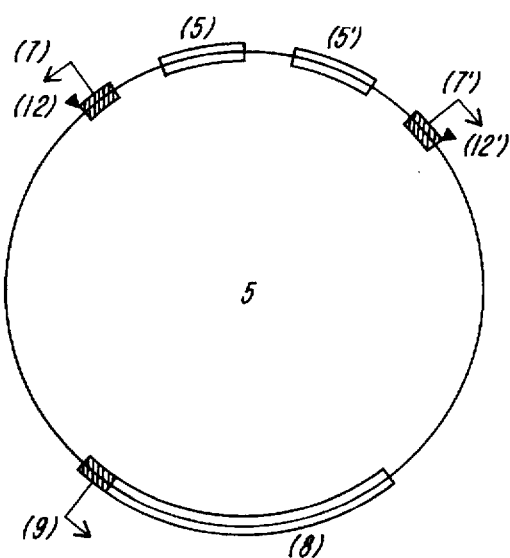

FIGS. 5 and depict illustrative embodiments of still other vectors of the invention. The vector of FIG. 5 is similar to that illustrated in FIG. 4 except that in place of the genes encoding proteins 6 and 6', DNA comprising specific restriction sites 12 and 12' is disposed adjacent the 3' ends of the promoters 7 and 7'. The vector of FIG. 6 features a blocking element 10 and other elements similar to the arrangement shown in FIG. 2, with its 3' end of the blocking element disposed adjacent the enhancer. In place of the gene 6 shown in FIG. 2, disposed adjacent the 3' end of promoter 7, is DNA comprising a restriction site 12.

Figure 6:
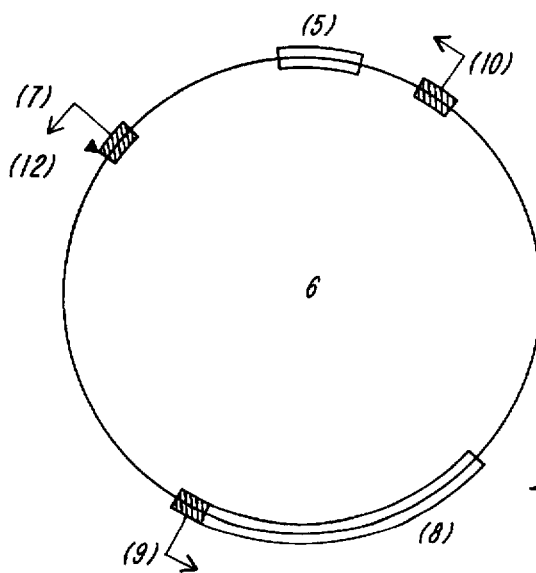

Vectors of the type illustrated in FIGS. 5 and 6 may be used to produce various transformants by first ligating a gene for a desired product into the restriction sites 12 or 12', amplifying the vector to produce plural clones, and then transfecting a suitable cell line.

The currently preferred vectors of the invention comprise cellular enhancer elements which are active in the genome of lymphoid cells. A preferred enhancer is the IgH enhancer (Gillies et al, supra). The vectors may be used to transfect myeloma cells of murine origin such as cell line J558 (ATCC TIB 6), Sp2/0-Ag14 (ATCC CRL 1581), and P3X63-Ag8.653 (ATCC CRL 1580). The preferred marker region for use in the vectors is the gpt gene flanked on its 5' side by the SV40 promoter and viral enhancer and on its 3' side by the SV40 intervening sequence and poly A+ addition site. It should be noted that activity of the SV40 viral enhancer in lymphoid cells is much less than the activity of the IgH enhancer. Therefore, it is desirable to prevent enhancement by the cellular enhancer on the gpt gene to achieve high expression of the gene of interest, but unnecessary to prevent enhancement by the SV40 viral enhancer on the gpt gene.

Using the vectors of the invention, high level expression of several cDNAs have been achieved, including expression of human tissue plasminogen activator (TPA). Transfection of the vectors can result in isolation of stably transformed cells which consistently exhibit increased levels of transcription of the gene encoding the protein of interest.

In a separate but related development, another mechanism employed by animal cells to achieve high level expression has been discovered. It was noted that the 3' untranslated regions (3'UTs) of the highly abundant immunoglobulin mRNAs in lymphoid cells are relatively short (less than about 200 nucleotides), whereas the 3' UTs of several genes of interest not expressed at high levels in normal lymphoid cells are relatively long. For example, the 3' UT of TPA is approximately 800 nucleotides long (Pennica et al, Nature, V. 301, 214–231, January, 1983), that of Factor VIII is about 1800 nucleotides (Wood et al, Nature, V. 312, 330–337, November, 1984), and that of erythropoietin is about 560 nucleotides (Jacobs et al, Nature, V. 313, 806–810, February, 1985). This observation has been exploited to increase the stability of mRNA transcribed from exogenous genes in lymphoid cells by replacing the long 3' UTs with short 3' UTs. The short 3' UT region must still provide the necessary information for mRNA processing at the 3' end, such as the polyadenylation addition signal and flanking sequences.

The substitution of 3' UTs is accomplished by truncating the exogenous gene (or cDNA) at a point beyond its translation stop signal and ligating it to an excised, short 3' UT region from, for example, an immunoglobulin gene or the SV40 early region gene. The "fused" DNA results in fused mRNA of increased intracellular stability.

The combination of selective enhancement as disclosed herein to increase levels of transcription and exploitation of the 3' UT to promote mRNA stability results in clones with very high levels of expression. For example, high level expression of the TPA cDNA has been achieved in lymphoid cells by removing all except 34 nucleotides of the 800 nucleotide long 3' UT region and replacing it with the short (approximately 200 nucleotide) 3' UT region from either SV40 or the C Kappa immunoglobulin gene.

The invention will be further understood from the following nonlimiting example.

The invention was used to obtain transformed mouse myeloma cells expressing high levels of the human thrombolytic enzyme tissue plasminogen activator (TPA). The TPA cDNA was inserted into an expression vector which contained the murine immunoglobulin heavy chain (IgH) enhancer, the metallothioneine (MT) promoter, and the *E. coli* gpt gene. The enhancement of the gpt gene by the IgH enhancer was blocked by the insertion of the murine immunoglobulin lambda light chain promoter into the vector.

Figure 7:
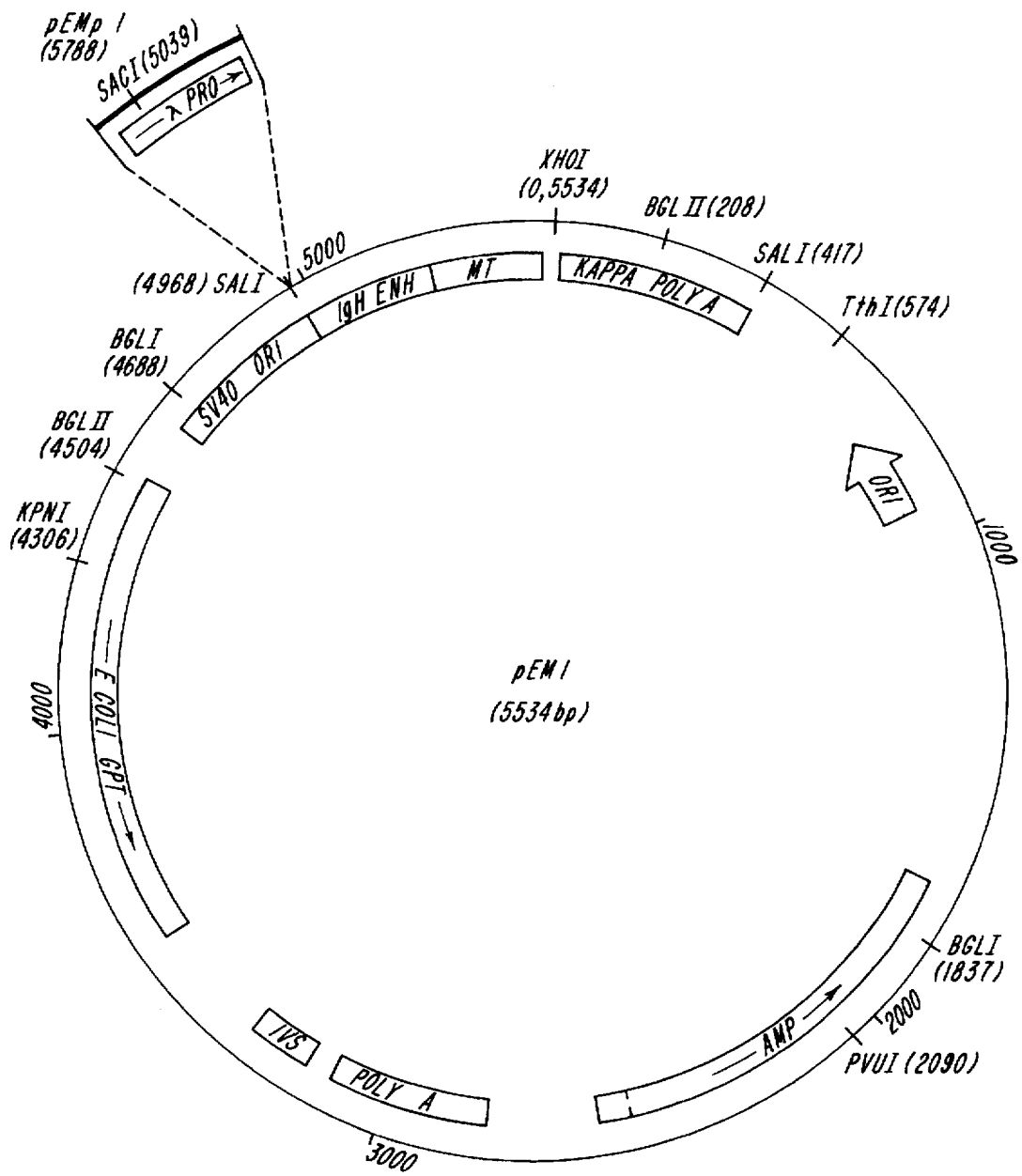
FIG. 7 is a diagram of vector pEM1 which was used to construct a preferred vector of the invention.

The basic expression vector, pEM1, is diagrammed in FIG. 7. It was constructed from the following fragments: (a) a 2.25 PvuII-BamHI fragment from pSV2-gpt (Mulligan and Berg, Science; V. 209, 1422–1427, 1980) containing the SV40 enhancer and early region promoter, the *E. coli* gpt gene, the SV40 small tumor-antigen intervening sequence, and the SV40 transcription termination and polyadenylation signals; (b) a 2.3 kb PvuII-EcoRI fragment from pBR322 containing the ampicillinase gene and the bacterial origin of replication (Sutcliffe, Proc. Natl. Acad. Sci. USA, V. 75, 3737, 1978); (c) a 0.3 kb PvuII-EcoRI fragment containing the immunoglobulin heavy chain enhancer (Gillies et al. Cell, supra, 1983); (d) a 0.25 kb SacI-BglII fragment containing the metallothioneine I promoter (Brinster et al, Nature, V. 296, 39–42, 1982); and (e) a 0.4 kb AvaII-HaeIII fragment from the 3' UT region of the immunoglobulin kappa light chain gene, which includes the polyadenylation signal (Max et al, J. Biol. Chem., V. 256,5116–5120, 1981). These fragments were ligated together in a series of reactions according to well known methodologies (see, e.g., Maniatis et al, *Molecular Cloning: A Laboratory Manual*, Cold Spring Harbor, 1982).

The vector pEMpl (FIG. 7) was constructed by inserting an enhancer-blocking element into pEM1. A 0.26 kb XbaI-BstNI fragment containing the immunoglobulin light chain promoter, the TATAA sequence, the transcription initiation site, and the first 22 nucleotides thereafter, was blunt-end ligated into the SalI site located at one end of the IgH enhancer segment.

The cDNA for TPA was obtained by standard techniques (Maniatis, supra). PolyA+ RNA isolated from cultured Bowes cells was primed with oligo (dT) for first strand synthesis with reverse transcriptase, nick-translated with RNase H and DNA polymerase I for second strand synthesis (Gubler & Hoffman, Gene, V. 25, 263, 1983), methylated with EcoRI methylase, ligated to EcoRI linkers, and inserted into the EcoRI site of the lambda phage vector gt10. Phage plaques were screened with radioactively labelled oligonucleotide TPA-specific probes, the sequences of which were determined from the published DNA sequence of the TPA cDNA (Pennica et al, supra). TPA clones containing the entire coding region, and approximately 800 base pairs of the 3' UT region were identified and confirmed by nucleotide sequencing.

The extremely long 3' UT region of the TPA cDNA was discovered to cause messenger RNA instability. The bulk of the 3' UT region was therefore eliminated by cleaving at the Sau3A site located 34 nucleotides downstream of the translation stop site. A 1.7 kb fragment containing the TPA cDNA with the truncated 3' UT was ligated to XhoI linkers.

Figure 8:
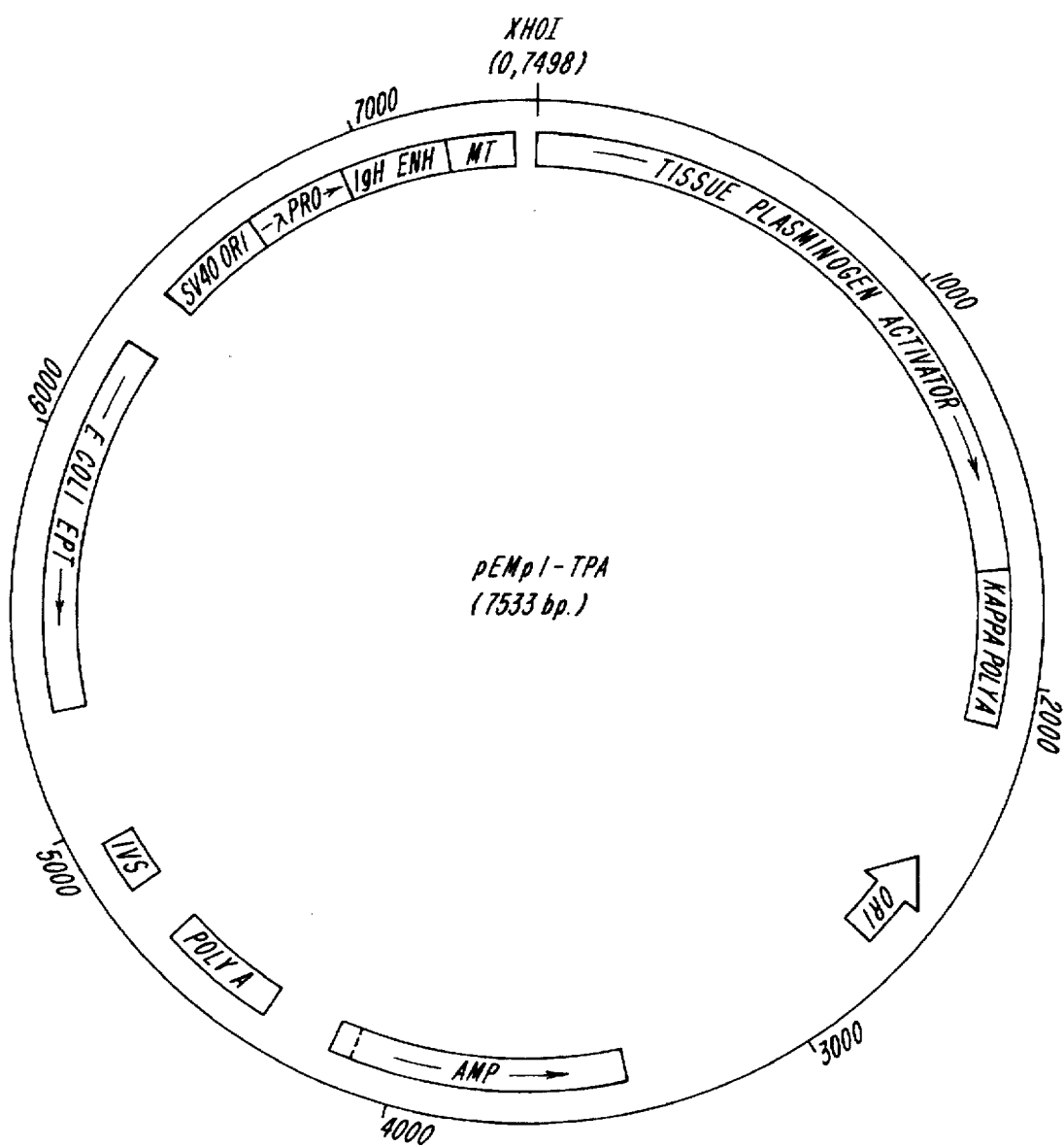
FIG. 8 is a diagram of vector pEMlpl-tpa for use in expressing TPA in myeloma cells. This vector represents the currently preferred embodiment of the invention. The TPA gene was inserted as an example of a gene that may be expressed at high levels in this and other embodiments of the invention.
Figure 9A:
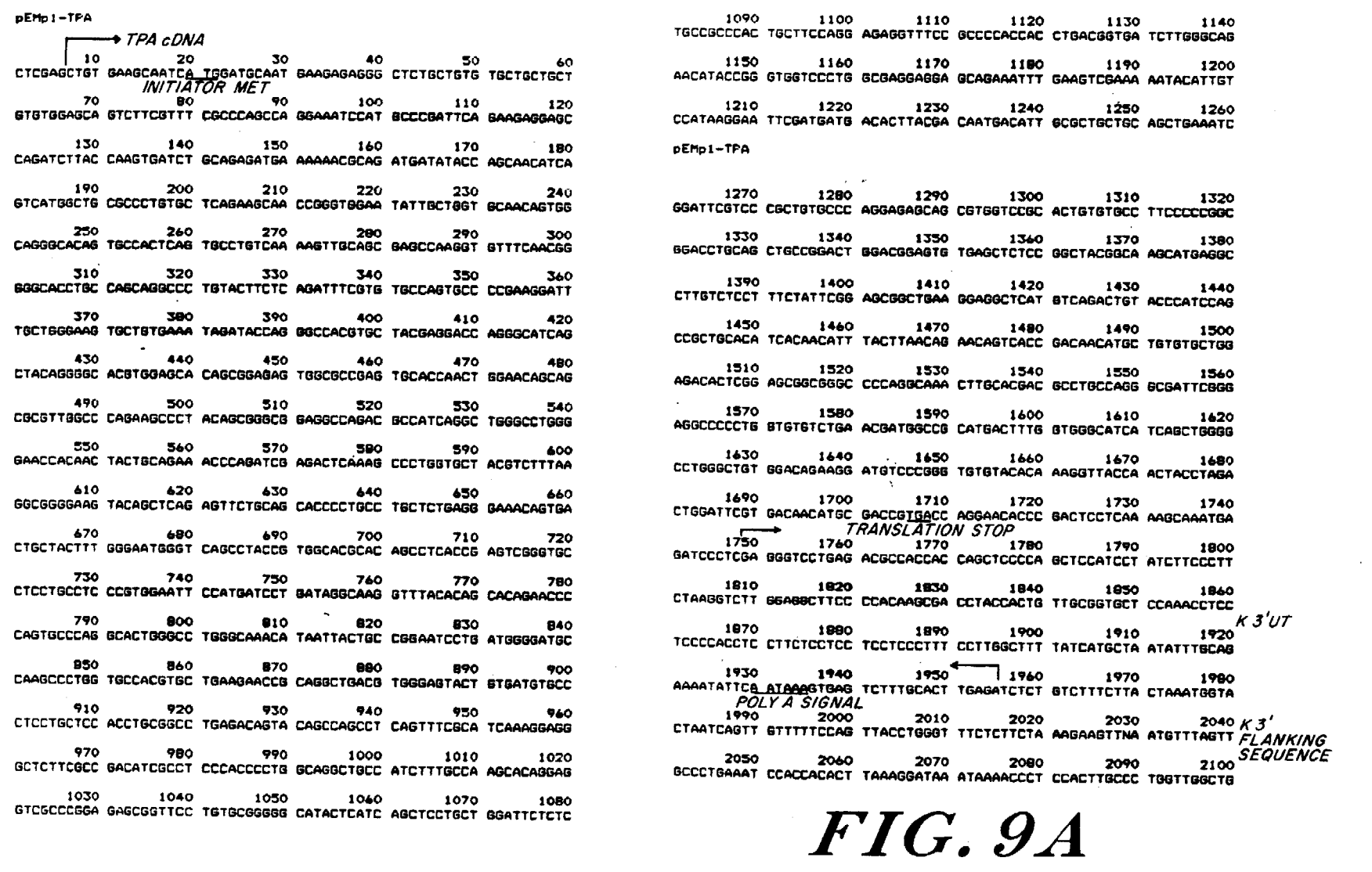
Figure 9B:
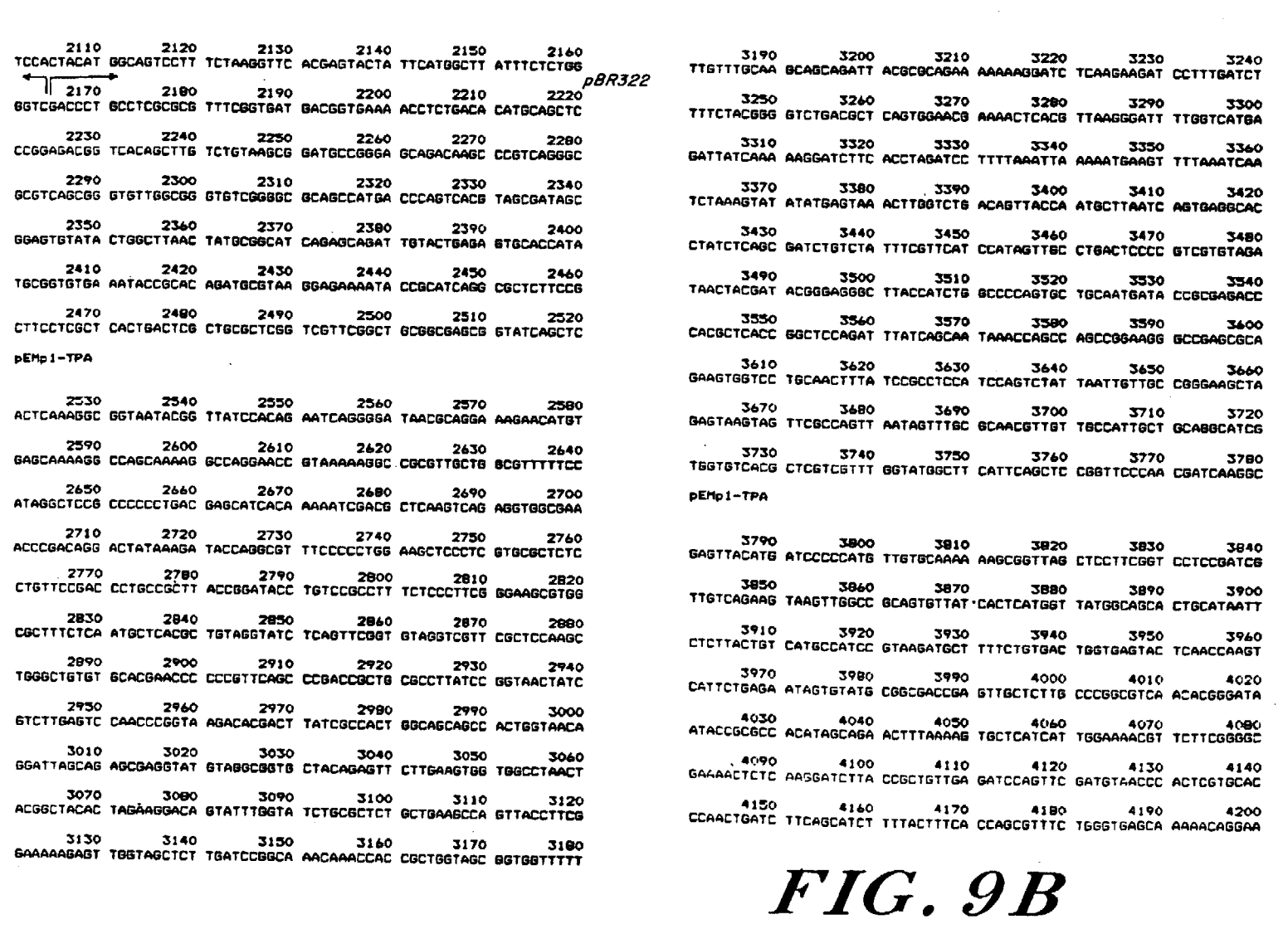
Figure 9C:
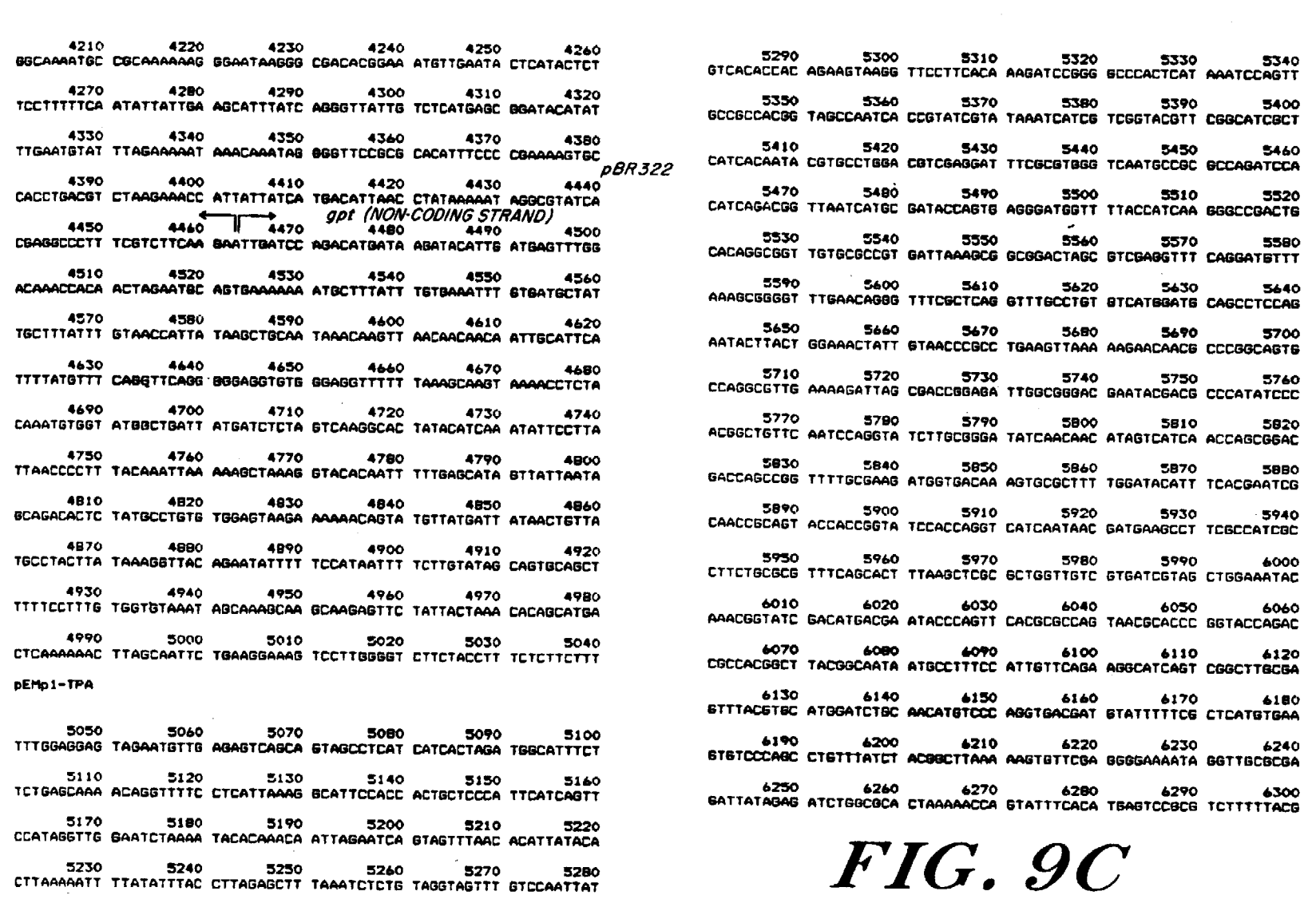
Figure 9D:
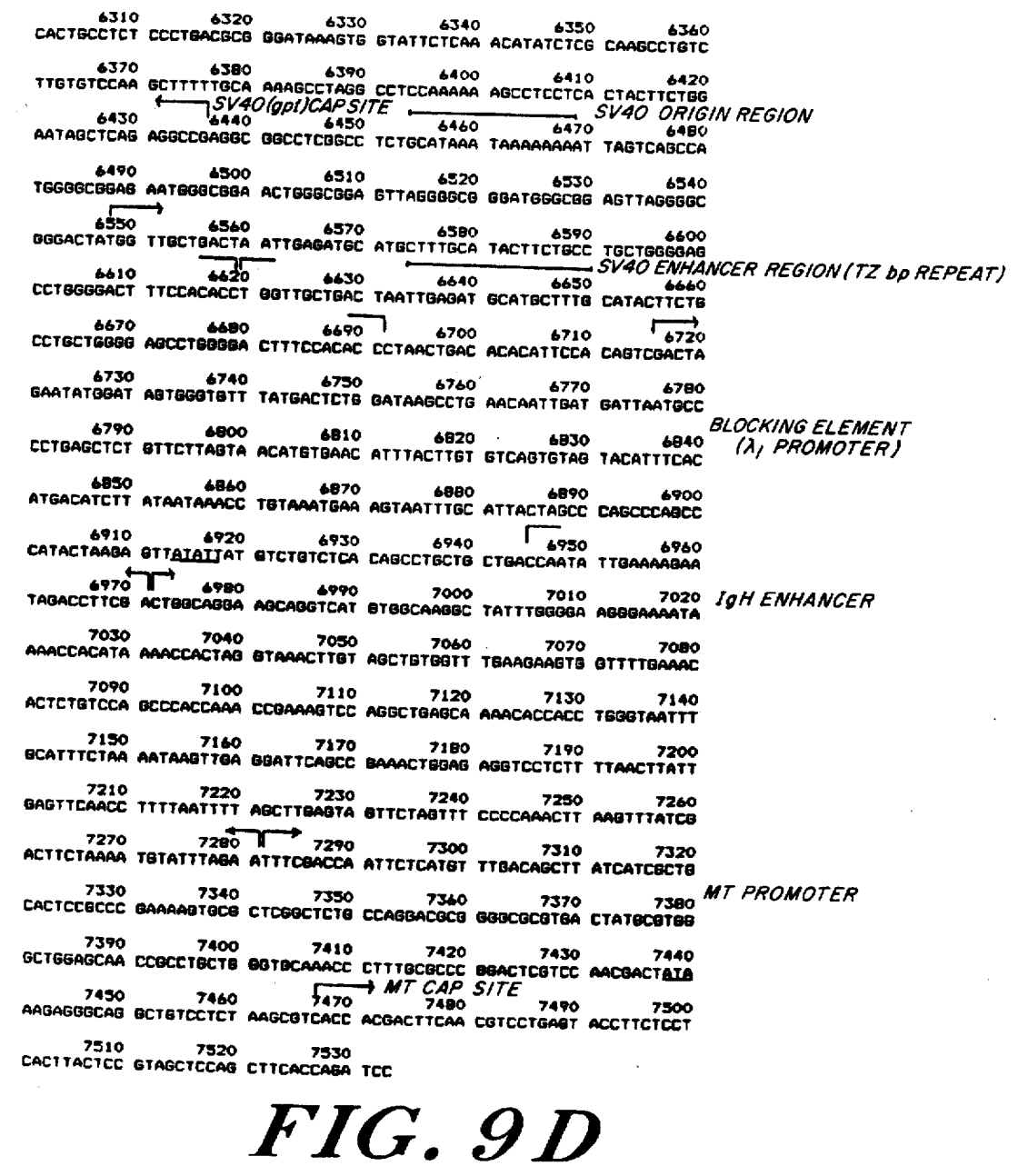

The TPA cDNA fragment was inserted into the unique XhoI site present in both pEM1 and pEMpl to produce recombinant plasmids, pEM1-tpa and pEMpl-tpa. A diagram of vector pEMpl-tpa is given in FIG. 8; the complete nucleotide sequence of the vector is disclosed in FIGS. 9A–9D. The map and sequence of the second TPA vector, pEM1-tpa, differs from that given in FIGS. 8 and 9A–9D only in that pEM1-tpa lacks the lambda promoter blocking element.

The TPA-containing plasmids were transfected into J558L myeloma cells by the protoplast fusion method (Gillies et al, supra). Cells containing either plasmid, and therefore the gpt gene, were selected by culturing in media containing mycophenolic acid. Resistant colonies containing pEM1-tpa and resistant colonies containing pEMpl-tpa were subcloned and screened for TPA expression. The synthesis and secretion of TPA into the medium was determined by means of an assay in which TPA converts plasminogen to plasmin, which then cleaves the chromogenic tripeptide S2251 (Pennica et al, supra). Because it is known that serum contains inhibitors of both TPA and plasmin (Collen and Lijnen, CRC Critical Reviews in Oncology/Hematology, V. 4, 249–301, 1986), transformants were cultured for 48 hours in serum-free medium before assay. Activity was measured in international units (IU) based on a standard supplied by the World Health Organization and confirmed by a TPA standard obtained from American Diagnostics, Inc.

As explained above, not all transformants are expected to produce TPA because of possible disruption of the TPA gene during vector integration. Twenty-six of the transformants obtained with vector pEM1-tpa were assayed for the presence of TPA in the culture supernatant. As indicated in the table below, 5 of the 26 produced TPA at levels ranging between 140 and 500 IU/ml. Sixteen of the transformants obtained with pEMpl-tpa, i.e., the vector with the enhancer-blocking element, were assayed for TPA activity in the medium. Seven of the 16 were positive, with activities ranging between 1000 and 6000 IU/ml. Thus, the presence of the IgH enhancer-blocking element in plasmid pEMpl-tpa resulted in cell transfectants which produced and secreted significantly higher levels of biologically active TPA.

TABLE

Expression of TPA by Transformed Cells

| Transfecting Vector | No. of Clones Tested | No. of Positive Clones | TPA concentration Range (IU/ml) |
|---|---|---|---|
| pEM1-tpa | 26 | 5 | 140–500 |
| pEMpl-tpa | 16 | 7 | 1000–6000 |

Figure 10:
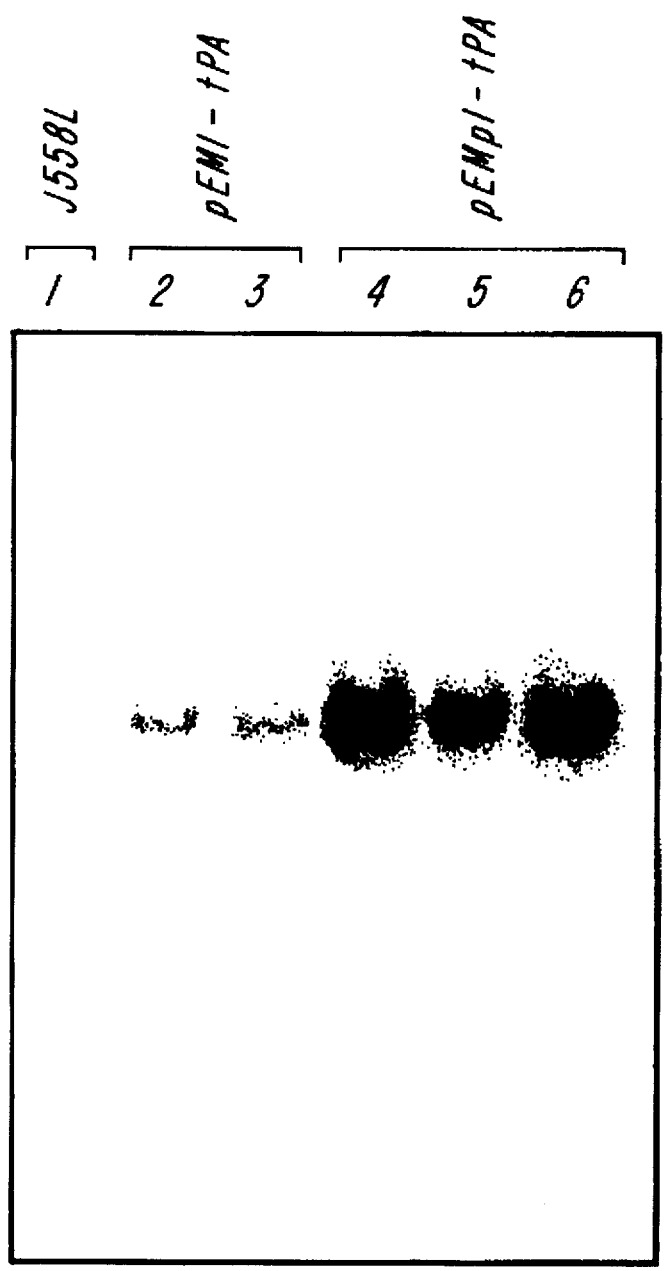
FIG. 10 is a Northern blot in which total cytoplasmic RNA isolated from control J558L cells, and the same cells transformed with either pEM1-tpa or pEMpl-tpa vector DNA was analyzed for the presence of TPA specific RNA.

The levels of TPA mRNA obtained with and without the IgH enhancer-blocking element were consistent with the activity levels. Cytoplasmic RNA was isolated from the 2 or 3 clones from each group that secreted the highest levels of TPA. The RNA samples were analyzed for TPA-specific mRNA by Northern blotting and hybridization. As shown in FIG. 10, the relative levels of TPA mRNA were significantly higher (approximately 5 to 10 fold) in cells transfected with plasmid pEMpl-tpa versus cells transfected with plasmid pEM1-tpa.

The invention may be embodied in other specific forms without departing from the spirit and scope thereof.

What is claimed is:

1. An isolated animal cell transfected with a vector, said vector comprising:

(a) a selectable marker gene comprising a promoter operatively linked to a nucleic acid encoding a selectable marker enzyme;

(b) a first transcription unit comprising a promoter operatively linked to a nucleic acid encoding a first protein;

(c) a first enhancer located between the selectable marker gene and the first transcription unit, which first enhancer stimulates transcription of both the selectable marker gene and the first transcription unit compared to the transcription of both the selectable marker gene and the first transcription unit in the absence of the first enhancer; and (d) a blocking element comprising a promoter interposed between the first enhancer and the selectable marker gene, which blocking element selectively attenuates the stimulation of transcription of the selectable marker gene.

2. The isolated animal cell of claim 1, wherein said blocking element is oriented with the transcription promoted by the blocking element promoter directed towards the enhancer.

3. The isolated animal cell of claim 1, wherein said vector further comprises a second transcription unit comprising a promoter operatively linked to a nucleic acid encoding a second protein, which second transcription unit is located between said first enhancer and said blocking element.

4. The isolated animal cell of claim 3, wherein said first protein and said second protein are the same protein.

5. The isolated animal cell of claim 3, wherein said vector further comprises a second enhancer, which second enhancer is located between the first enhancer and the second transcription unit and said second enhancer stimulates transcription of said second transcription unit compared to the transcription of said second transcription unit in the absence of said second enhancer.

6. The isolated animal cell of claim 3, wherein said first protein or said second protein is selected from the group consisting of cytokines, immunoglobins, hormones, and enzymes.

7. The isolated animal cell of claim 3, wherein said first protein or said second protein is a plasminogen activator selected from the group consisting of human prourokinase and human tissue plasminogen activator.

8. A method of manufacturing an isolated animal cell transfected with a vector, said method comprising:

(a) transfecting an animal cell with the vector, said vector comprising:

(i) a selectable marker gene comprising a promoter operatively linked to a nucleic acid encoding a selectable marker enzyme which enables the animal cell to survive in a medium containing a compound normally toxic to the animal cell;

(ii) a transcription unit comprising a promoter operatively linked to a nucleic acid encoding a protein;

(iii) an enhancer located between the selectable marker gene and the transcription unit, which enhancer stimulates transcription of both the selectable marker gene and the transcription unit compared to the transcription of both the selectable marker gene and the transcription unit in the absence of the enhancer; and (iv) a blocking element comprising a promoter interposed between the enhancer and the selectable marker gene, which blocking element selectively attenuates the stimulation of transcription of the selectable marker gene;

(b) culturing an animal cell resulting from step (a) in a medium containing the compound normally toxic to the animal cell; and (c) isolating an animal cell resulting from step (b) which expresses the protein.

9. An expression vector comprising:

(a) a selectable marker gene comprising a promoter operatively linked to a nucleic acid encoding a selectable marker enzyme;

(b) a transcription unit comprising a promoter operatively linked to a nucleic acid encoding a protein;

(c) an enhancer located between the selectable marker gene and the transcription unit, which enhancer stimulates transcription of both the selectable marker gene and the transcription unit compared to the transcription of both the selectable marker gene and the transcription unit in the absence of the enhancer; and (d) a blocking element comprising a promoter interposed between the enhancer and the selectable marker gene, which blocking element selectively attenuates the stimulation of transcription of the selectable marker gene.

* * * * *